United States Patent [19]

Hettche

[11] Patent Number: 5,271,946

[45] Date of Patent: Dec. 21, 1993

[54] CONTROLLED RELEASE AZELASTINE-CONTAINING PHARMACEUTICAL COMPOSITIONS

[75] Inventor: Helmut Hettche, Dietzenbach, Fed. Rep. of Germany

[73] Assignee: Asta Pharma Aktiengesellschaft, Fed. Rep. of Germany

[21] Appl. No.: 865,769

[22] Filed: Apr. 10, 1992

Related U.S. Application Data

[63] Continuation of Ser. No. 340,694, Apr. 20, 1989, abandoned.

[30] Foreign Application Priority Data

Apr. 20, 1988 [DE] Fed. Rep. of Germany ....... 3813244

[51] Int. Cl.$^5$ .......................... A61K 9/16; A61K 9/22; A61K 9/28; A61K 9/54
[52] U.S. Cl. .................................. 424/490; 424/465; 424/457; 424/458; 424/467; 424/422; 424/468; 424/473; 424/474; 424/475; 424/483; 424/499; 424/502; 514/826
[58] Field of Search ............... 424/473, 469, 483, 468, 424/490; 514/826

[56] References Cited

U.S. PATENT DOCUMENTS

| | | | |
|---|---|---|---|
| 4,704,285 | 11/1987 | Alderman | 424/468 |
| 4,704,387 | 11/1987 | Engel et al. | 544/357 |
| 4,829,064 | 5/1989 | Sunshine et al. | 514/290 |
| 4,853,249 | 8/1989 | Takashima et al. | 424/468 |
| 5,086,050 | 2/1992 | Hettche et al. | 514/887 |

Primary Examiner—Paul R. Michl
Assistant Examiner—James M. Spear
Attorney, Agent, or Firm—Cushman, Darby & Cushman

[57] ABSTRACT

Azelastine-containing pharmaceutical compositions which provide controlled release of the active substance using a sustained release component. The compositions contain azelastine or a physiologically acceptable salt of azelastine, together with 0.001 to 800 parts of sustained release component for each part by weight of azelastine (calculated as base) and the release rate of azelastine is between 0.05 and 5 mg per hour.

6 Claims, No Drawings

CONTROLLED RELEASE AZELASTINE-CONTAINING PHARMACEUTICAL COMPOSITIONS

This is a continuation of application Ser. No. 07/340,694, filed on Apr. 20, 1989, which was abandoned.

The present invention relates to pharmaceutical compositions with a controlled release of azelastine.

BACKGROUND OF THE INVENTION

Azelastine is a phthalazinone derivative having the following structural formula:

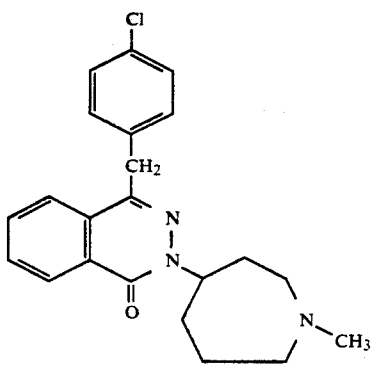

The chemical designation is: 4-(4-chlorobenzyl)-2-(perhydro-1-methylazepine-4-yl)-1-(2H) phthalazinone. Azelastine is used in particular in asthma prophylaxis. Azelastine also has anti-allergic and antihistaminic properties, see German Patent No. 21 64 058.

One of the main disadvantages of using azelastine is that it makes the patients tired. Many patients also report drowsiness, giddiness and the like. These side effects develop especially during the first days of azelastine therapy, and preclude the patients from operating motor vehicles or machinery. There is a general loss of alertness.

Therefore, it would be highly desirable, and would be regarded as an important medical advance, if azelastine could be administered to patients which did not cause these side effects.

In the past, these side effects have been conventionally alleviated by supplying a combination medication which contained both the active substance which made the patient tired and caffeine. The caffeine was intended to antagonize the sedative property of the active substance. However, this procedure cannot be used in the case of azelastine since the elimination half lives $t_{\frac{1}{2}}$ ($t_{\frac{1}{2}}$ is the time within which the serum level of the active substance in the blood diminishes without further active substance intake from a specific starting value to half this value) of azelastine and caffeine differ very greatly from one another: the $t_{\frac{1}{2}}$ of azelastine is 20 hours whereas the $t_{\frac{1}{2}}$ of caffeine is only 3.5 hours. Therefore, it is to be expected that, if azelastine and caffeine are administered together, the effect of the caffeine will decrease after a certain time, and the sedative effect of the azelastine will once again become apparent.

The conventional approach is then to delay the release of the active substance—caffeine—in the dosage form so much that a prolonged time of efficacy results. This procedure is, however, linked with the difficulty of adjusting the blood level rates of the two active substances in vivo so that they are as similar as possible. This is not possible, using techniques presently available, because of the large differences in the elimination rates.

A further problem with azelastine is its extremely unpleasant taste. The taste is so unpleasant that, for example, liquid azelastine formulations (for example juice) are not taken, or even refused, by patients, in particular by children.

SUMMARY OF THE INVENTION

It is the object of the present invention to provide a pharmaceutical composition containing the active substance azelastine which significantly reduces or completely eliminates the sedative effect of azelastine and which has a more acceptable taste. The invention also provides a process for the preparation of such composition.

These and other objects are achieved by a pharmaceutical composition which provides controlled release of the active substance. The composition contains conventional auxiliary substances and additives and a sustained release component which is characterized in that the active substance, azelastine, or its physiologically acceptable salts, are released in a controlled manner. A dosage unit of the composition contains 0.001 to 800 parts by weight of sustained release components are present together with each 1 part by weight of azelastine calculated as base. The composition is formulated so that the release rate is 0.05 to 5 mg, for example 0.05 mg to 3 mg or also 0.05 mg to 1 mg of azelastine per hour.

If the azelastine is present in the form of a salt, the above mentioned amounts of azelastine which relate to the base are correspondingly increased to take into account the higher molecular weight of the salt. The amounts of 'azelastine' quoted in this description relate in all cases to the base and must be recalculated according to the increased molecular weight when a salt is used.

The present invention also provides a process for the preparation of a drug formulation with controlled release of the active substance by incorporation of an active substance in conventional auxiliary and ancillary substances and a sustained release component which is characterized in that azelastine or its physiologically acceptable salts are used as the active substance to be released in a controlled manner in the ratio of 1 part by weight of azelastine, calculated as base, to 0.001 to 800 parts by weight of the sustained release component whereby the azelastine is released at a rate of 0.05 to 5 mg per hour.

It has been found surprisingly that it was not necessary to add caffeine, either in sustained release or non-sustained release form, in order to obtain a dosage form of azelastine which does not cause the side effect of tiredness, but that it suffices to delay the release of the active substance azelastine itself. Thus, if the active substance azelastine is brought into a dosage form which releases the active substance over a longer period of time (and thereby effects a 'retardation' of the active substance), it is found that patients treated with this dosage form no longer experience the side effect of tiredness. This is particularly surprising in view of azelastine's previously mentioned elimination half life of 20 hours.

The process of sustained release has only been used in pharmaceutical technology on substances with short half lives, e.g. of up to a maximum of 10 hours. The sustained release of an active substance which has a half life of 20 hours has to date been regarded by pharmaceutical science virtually as serving no useful purpose.

It is also surprising that the bitter taste hitherto observed after intake does not occur with the dosage forms of the present invention.

The present invention thus relates to dosage forms with controlled release of the active substance azelastine or of physiologically acceptable salts of azelastine. Suitable salts are, for example, chloride, acetate, maleinate, lactate, citrate, tartrate, gluconate, embonate.

The release rate for azelastine from the compositions of the invention may be determined in an aqueous solution having a pH of 0.5 or a pH of 6.8, the pH being controlled by addition of acid or a conventional buffer. Compositions whose release rate is 0.05 to 5 mg per hour in such solutions are suitable for the purposes of the invention.

Dosage forms that may, for example, be considered are: sustained release tablets, sustained release capsules, pellets, juices, implants, injections, plasters, aqueous or oily suspensions, oily solutions, granulates, coated tablets, soft gelatin capsules, microcapsules.

The formulations of the invention may be obtained as follows:

1. Through binding of azelastine to physiologically acceptable cation exchangers. The following may, for example, be used as such cation exchangers:

Acrylic and methacrylic resins with exchangeable protons, acid groups: $COO^-$ e.g. Amberlite ® IRP-64 Polystyrene resins with exchangeable $Na^+$, acid groups: $SO_3^-$, e.g. Amberlite ® IRP-69

The ion exchangers are acid ion exchangers. The maximum ratio of azelastine:exchange resin is about 1:1, the minimum ratio about 1 part by weight of active substance to 800 parts of ion exchanger resin. Preferably, 1 to 400 parts by weight of ion exchanger are used for 1 part by weight of active substance, 1 to 100 parts by weight of ion exchanger being quite particularly preferred.

The binding of the azelastine is effected by allowing an azelastine solution to flow through a bed of the ion exchanger in a column or by suspending the ion exchanger in a solution of azelastine, filtering off after stirring and washing. The charged ion exchanger is dried at temperatures up to about 50° C.

The charged ion exchanger particles are preferably also provided with a coating such as described for example in U.S. Pat. No. 4,221,776. One advantage of the additional coating is that the release rate of the active substance may be altered and influenced by the selection of the coating material. The charged ion exchanger particles provided with a coating may be dried with hot air at from 70° C. to 90° C.

The charged ion exchanger particles may be filled into hard gelatin capsules or a suspension may be prepared as a liquid dosage form with the aid of water and thickening agents, flavoring and stabilizing agents and preservatives.

2. Coating of active ingredient particles, granulate or pellet grains or azelastine-containing tablets with coatings of the following substances, or mixtures of the following substances:

hydroxypropylmethyl cellulose phthalate- or acetate succinate; cellulose-, starch-, as well as polyvinyl acetate phthalate; carboxymethyl cellulose; polyvinyl acetate; methylcellulose phthalate, methylcellulose succinate, methyl cellulose phthalate succinate as well as methyl cellulose phthalic acid half ester; zein; ethyl cellulose as well as ethyl cellulose succinate; shellac; gluten; ethylcarboxyethyl cellulose; ethacrylate- maleic acid anhydride copolymer; maleic acid anhydride vinyl methyl ether copolymer; styrol maleic acid copolymerizate; 2-ethylhexylacrylate maleic acid anhydride; crotonic acid vinyl acetate copolymer; glutaminic acid / glutaminic acid ester copolymer; carboxymethylethyl cellulose glycerin mono-octanoate; cellulose acetate succinate; polyarginin; fats, oils, waxes, fatty alcohols; anionic polymerizates of methacrylic acid and methacrylic acid esters (Eudragit ®L, Eudragit ®S); copolymerizates of acrylic and methacrylic acid esters with a low ammonium group (Eudragit ®RS) content, as well as copolymers of acrylic and methacrylic acid esters and trimethyl ammonium methacrylate (Eudragit ®RL), copolymerizates of acrylic acid ethyl- and methacrylic acid methyl esters 70:30 (Eudragit ®NE 30 D), copolymerizates of acrylic acid, methacrylic acid as well as their esters (ratio of the free carboxyl groups to the ester groups for example 1:1) (Eudragit ®L 30 D).

The substances named may also contain conventional softeners (e.g. dibutyl sebacate, citric and tartaric acid esters, glycerin and glycerin esters, phthalic acid esters and similar substances). It also is possible to add water-soluble substances such as polyethylene glycols, polyvinylpyrrolidone, copolymerizates of polyvinylpyrrolidone and polyvinyl acetate, hydroxypropyl cellulose, hydroxypropylmethyl cellulose. The addition of solids such as talcum and/or magnesium stearate to the coating is also possible.

Organic acids (such as for example citric acid, tartaric acid, maleic, fumaric, ascorbic acid) may also be incorporated into the pellet grains, granulate grains or tablets.

Coating is effected by spraying solutions of the foregoing substances in organic solvents or suspensions of those substances in organic solvents or water. It also is possible to add further auxiliary substances to optimize their processability, such as for example surface-active substances and pigments.

The spraying is effected for example in a coating drum or in perforated drums or in an air suspension process (for example Glatt WLSD5 fluidized air bed installation).

Coating may also take place using a coacervation process in which so-called microcapsules are formed.

Coating may also be effected by coagulation of aqueous dispersions of the previously mentioned substances by mixing the active substance with the dispersion and removing the water by drying.

Coated active substance particles and coated granulates may be pressed into tablets, coated pellets may be filled into hard gelatin capsules.

In coating the active substance particles or granulates which contain active substance particles, more coating substance is generally used than in the case of pellets since the surface which must be covered is considerably larger than in the case of pellets.

It is possible to use 0.001 to 800 parts by weight of coating substance for 1 part by weight of active substance. A weight ratio of 1 part of active substance and 0.005 to 500 parts by weight of coating material is preferred, 0.01 to 200 parts by weight of coating material per 1 part by weight of active substance being quite particularly preferred. The application of the coating substances is effected at elevated temperature, preferably in a flow of air. Air inlet temperature for example 70° to 90° C.; air outlet temperature for example up to 40° C.

3. Coating of pressed disks, tablets, granulates containing the azelastine and one or more osmotically active substances, (e.g. mannitol, sorbitol) with a semi-permeable membrane, e.g. of 70 to 90 weight% of cellulose acetate and hydroxypropylmethyl cellulose (30 to 10 weight%).

Osmotically active substances which may also be considered are: organic and inorganic compounds or soluble substances which generate an osmotic pressure gradient as compared to the outer liquid via the semi-permeable wall. Osmotically active agents or osmotically active compounds comprise magnesium sulfate, magnesium chloride, sodium chloride, lithium chloride, potassium sulfate, potassium hydrogen phosphate, urea, saccharose and the like. Other osmotically active agents are known from U.S. Pat. Nos. 3,854,770, 4,077,407 and 4,235,236.

Semi-permeable materials which are known as polymers for osmosis and reverse osmosis are, for example: cellulose acylate, cellulose diacylate, cellulose triacylate, cellulose acetate, cellulose diacetate, cellulose triacetate, β-glucan acetate, acetaldehyde dimethyl acetate, cellulose acetate ethyl carbamate, polyamide, polyurethane, sulphonated polystyrene, cellulose acetate phthalate, cellulose acetate methyl carbamate, cellulose acetate succinate, cellulose acetate dimethylamino acetate, cellulose acetate chloracetate, cellulose dipalmitate, cellulose dioctanoate, cellulose dicaprylate, cellulose dipentanate, cellulose acetate valerate, cellulose acetate-p-toluene sulphonate, cellulose acetate butyrate, ethyl cellulose, selectively permeable polymers which are formed by joint precipitation of a polycation and a polyanion as set out in U.S. Pat. Nos. 3,173,876, 3,276,586, 3,541,005, 3,541,006 and 3,546,142. Coatings of this type in semi-permeable membranes may for example also be effected according to published German patent applications DE-A-33 10 081 and DE-A-33 10 096.

The proportion of osmotically active substance can be from 10 to 800 parts by weight, preferably 20 to 600, and more preferably 50 to 400 parts by weight, based on 1 part by weight of azelastine. The amount of coating substances applied is such that the semi-permeable membrane is 50 to 500 μm, preferably 100 to 300 μm thick.

The processing of the active substance and the osmotically active substances may be effected between room temperature and 80° C. To adjust the release rate a hole is for example bored in the membrane wall, e.g. with the aid of a laser beam, so that, after addition of the tablets to an aqueous liquid, the active substance may be dissolved or suspended by liquid entering and then expressed out through the hole. The application of the semi-permeable layer is effected, for example, at an air inlet temperature of 70°–90° C.

The semi-permeable membrane may optionally also contain a microporous layer or microporous substances may be incorporated in the connection German Offenlegungsschrift 33 10 081 (see for example pages 7–17).

Materials which are suitable for the preparation of the microporous layer comprise for example polycarbonates of linear polyesters of carbonic acid in which carbonate groups recur in the polymer chain, microporous materials which have been prepared by phosgenation of a dihydroxy-aromatic compound such as bisphenol, a microporous polyvinyl chloride, microporous polyamides such as polyhexamethylene adipamide, microporous modacrylic polymers including those formed from polyvinyl chloride and acrylonitrile, microporous styrene acrylic monomers and their copolymers, porous polysulphones characterized by diphenylene sulphone in a linear chain, halogenated polyvinylides, polychloroether, acetal polymers, polyesters prepared by esterification of a dicarboxylic acid or an anhydride with an alkylene polyol, polyalkylene sulphides, phenolic polymers, polyesters, microporous polysaccharides with substituted anhydroglucose units having a decreasing permeability for water and biological fluids, asymmetric porous polymers, cross-linked olefin polymers, hydrophobic or hydrophilic microporous low density homopolymers, copolymers or interpolymers as well as materials which are described in the U.S. Pat. Nos. 3,595,752, 3,643,178, 3,654,066, 3,709,774, 3,718,532, 3,803,601, 3,852,224, 3,852,388 and 3,853,601; in British patent 1,126,849 and in Chemical Abstracts Volume 71, 427f, 22573f, 1969.

Other microporous materials for the preparation of the microporous layer include polyurethane, cross-linked chain-extending polyurethanes, polyimides, polybenzimidazoles, collodium, regenerated proteins, semi-solid cross-linked polyvinyl pyrrolidone, microporous materials which have been prepared by diffusion of polyvalent cations in polyelectrolyte salt water, microporous derivatives of polystyrene such as sodium polystyrene sulphonate, polyvinylbenzyl trimethyl ammonium chloride, microporous cellulose acylates and similar microporous polymers are known from U.S. Pat. Nos. 3,524,753, 3,565,259, 3,276,589, 3,541,055, 3,541,006, 3,546,142, 3,615,024, 3,646,178 and 3,852,224.

The pore forming agents suitable for the preparation of the microporous layer in the coating comprise solids and pore forming liquids. The term pore forming agents as used here also comprises substances which form micro passages and the range of the pore formers can lead to both types. The expression pore forming liquids within the scope of this description comprises semisolid and viscous liquids. The pore formers can be inorganic or organic and the layer forming polymer generally contains 5 to 70 weight% of pore forming agent, in particular 20 to 50 weight%. The term pore forming agent, as applied both to solids and to liquids comprises substances which can be dissolved, extracted or leached out of liquid present in the coating used from the precursor of the microporous membrane with the formation of an effective, open cellular microporous layer. The pore forming solids have a particle size of about 0.1 to 200 μm and comprise alkali salts such as lithium carbonate, sodium chloride, sodium bromide, potassium chloride, potassium sulfate, potassium phosphate, sodium acetate, sodium citrate and the like. Organic compounds such as saccharides including the sugars saccharose, glucose, fructose, mannitol, mannose, galactose, sorbitol and the like. For the coating used, one may also employ soluble polymers such as carbowaxes, Carbopol and the like. The pore forming agents also comprise diols, polyols, polyvalent alcohols, polyalkylene glycols, polyglycols, poly(α-∞) alkylene diols and the like.

4. Embedding of azelastine active substance or binding to the following substances or mixtures of these substances:

digestible fats, such as triglycerides of saturated fatty acids $C_8H_{16}O_2$ to $C_{18}H_{36}O_2$ and mixtures thereof, peanut oil and hydrated peanut oil, castor oil and hydrated castor oil, olive oil, sesame oil, cottonseed oil and hydrogenated cottonseed oil, corn oil, wheat germ oil, sunflower seed oil, cod liver oil, mixtures of mono-, di- and triesters of palmitic and stearic acid with glycerine, glycerine trioleate, diglycol stearate, stearic acid.

Indigestible fats or fat-like substances, for example esters of aliphatic saturated or unsaturated fatty acids (2 to 22 carbon atoms, in particular 10 to 18 carbon atoms) with monovalent aliphatic alcohols (1 to 20 carbon atoms), carnauba wax, beeswax, fatty alcohols (straight chain or branched) of chain length $C_8H_{17}OH$ to $C_{30}H_{61}OH$, in particular $C_{12}H_{25}OH$ to $C_{24}H_{49}OH$.

Polymers such as polyvinyl alcohol, polyvinyl chloride, polyacrylic acid (Carbopol®); anionic polymerizates of methacrylic acid and methacrylic acid esters (Eudragit®L, Eudragit®S), acrylic and methacrylic acid ester copolymerizates with trimethyl ammonium methacrylate (Eudragit®RL, Eudragit®RS).

Copolymerizates of ethyl acrylates and methyl methacrylates (Eudragit®NE 30 D), as well as of acrylic acid, methacrylic acid as well as esters thereof (ratio of free carboxyl groups to ester groups 1:1) (Eudragit®L 30 D), polyethylene, polyglycolic acid, polyhydroxybutyric acid, polylactic acid, copolymers of lactic acid and glycolic acid (manufacturer: Boehringer Ingelheim), copolymers of lactic acid and ethylene oxide, copolymers of glycolic acid and ethylene oxide, copolymers of lactic acid and hydroxybutyric acid, hydroxypropylmethyl cellulose- phthalate or -acetate succinate; cellulose acetate phthalate, starch acetate phthalate as well as polyvinyl acetate phthalate; carboxymethyl cellulose; methylcelulose phthalate, -succinate, -phthalate succinate, methyl cellulose phthalic acid half ester; zein; ethyl cellulose; shellac, gluten; ethylcarboxyethyl cellulose; ethacrylate maleic acid anhydride copolymer; maleic acid anhydride vinyl methyl ether copolymer; styrene maleic acid copolymerizate; 2-ethylhexyl acrylate maleic acid anhydride; crotonic acid vinyl acetate copolymer; glutaminic acid / glutaminic acid ester copolymer; carboxymethyl cellulose glycerine mono-octanoate; cellulose acetate succinate; polyarginine; cross-linked alginate; cross-linked gelatin;

Swelling agents such as methyl cellulose, hydroxypropyl cellulose, hydroxypropyl methyl cellulose (Pharmacoat, Methocel E=propylene glycol ether of methyl cellulose), alginic acid and their salts (Na-, Ca-salt, also mixtures of sodium alginate and calcium salts such as $CaHPO_4$), starch, carboxymethyl starch, carboxymethyl cellulose and their salts (e.g. Na-salts), galacto mannan, gum arabic, karaya rubber, ghatti gum, agar-agar, carrageen, xanthan rubber, guar rubber and its derivatives, carob bean flour, propylene glycol alginate, pectin, tragacanth.

In the case of these sustained release components 1 to 800 parts by weight of sustained release components are used per 1 part by weight of azelastine, preferably 1.5 to 600 parts by weight, 2.0 to 400 parts by weight being quite particularly preferred. The preparation of these formulations is effected at temperatures between 18° C. and 80° C. This dosage form may be prepared as follows:

a) by dissolving or dispersing azelastine or its salts in the fats or fat-like substances mentioned or in mixtures thereof, also by melting the substances mentioned with subsequent cooling, pulverizing, possibly adding other substances such as, for example, the above mentioned substances that are water soluble or swell in water and pressing into tablets. The cooling of the molten material and pulverizing can also be combined in one step by dispersing the melt in cold water or subjecting it to spray solidification. When the above mentioned oils are used as sustained release agents azelastine or its salt is dissolved or suspended in oil and, possibly after addition of up to 2% of aluminium monostearate, filled into ampoules and subsequently sterilized or homogenized and filled into bottles optionally after addition of flavorings and/or sedimentation retardants such as highly disperse silicon dioxide (e.g. Aerosil®).

b) by mixing azelastine with the fats, polymers or swelling agents referred to or mixtures of these substances, also with the application of heat, and pressing the mixtures, optionally after the addition of further auxiliary substances, into tablets or forming them into pellets.

c) by mixing azelastine with solutions of the fats or polymers referred to in water or organic solvents, such as for example ethanol, ethyl acetate, acetone or isopropanol, optionally mixing with carrier materials such as celluloses, as well as subsequent evaporation off of the solvents and mixing the embedded active substance obtained with additional auxiliary substances and processing into shapes such as, for example, tablets or pellets.

d) by moistening of a mixture of azelastine and the mentioned swelling agents with organic solvents such as ethanol, ethyl acetate, acetone or isopropanol, possibly with addition of binding agents such as polyvinyl pyrrolidone or copolymers of polyvinyl pyrrolidone and polyvinyl acetate, granulating the mixture obtained, then drying, optionally adding further auxiliary substances and pressing the mixture into tablets.

e) by mixing azelastine with a solution of natural or synthetic resins such as shellac or polyvinyl acetate in polyethylene glycol having a molecular weight of 200 to 1500, optionally adding further auxiliary substances such as for example stearates or swelling agents and encapsulating the material obtained into soft or hard gelatin capsules.

Generally speaking, the preparation of the drug formulations is effected in a manner known per se, the known and conventional pharmaceutical auxiliary substances being used in addition to the sustained release components as well as other conventional carrier and diluting agents, whereby the auxiliary substances mentioned as sustained release components may also fulfill other functions, for example as demolding agents or as disintegrating agents.

Carrier and auxiliary substances of this type may for example be those which are recommended or listed as auxiliary substances for pharmacy, cosmetics and related fields in the following literature references: Ullmanns Encyklopaedie der technischen Chemie, volume 4 (1953), pages 1 to 39; Journal of Pharmaceutical Sciences, volume 52 (1963), pages 918 et seq.; H. v. Czetsch-Lindenwald, Hilfsstoffe für Pharmazie und angrenzende Gebiete; Pharm. Ind. Issue 2, 1961, pages 72 et seq.; Dr. H. P. Fiedler, Lexikon der Hilfsstoffe für Pharmazie, Kosmetik und angrenzende Gebiete, 2nd edition, Editio Cantor, Aulendorf in Wuerttemberg 1981.

Examples of conventional auxiliary substances, carrier substances and diluting agents are gelatin, natural sugars such as raw sugar or lactose, lecithin, pectin, starch (e.g. corn starch), as well as starch derivatives, cyclodextrines and cyclodextrine derivatives, polyvinyl pyrrolidone, gum arabic, alginic acid, tylose, talcum, lycopodium, silica gel (e.g. colloidal), levulose, tragacanth, sodium chloride, stearate, magnesium and calcium salts of fatty acids with 12 to 22 carbon atoms, in particular the saturated acid (e.g. stearates), polyethylene glycol with a mean molecular weight between 200 and 20,000, preferably between 200 and 5,000, in particular between 200 and 1,000, or their mixtures and/or polymerizates of vinyl pyrrolidone and/or mixed polymerizates of vinyl pyrrolidone and vinyl acetate, esters of aliphatic saturated or unsaturated fatty acids (2 to 22 carbon atoms, in particular 10 to 18 carbon atoms) with monovalent aliphatic alcohols (1 to 20 carbon atoms) or polyvalent alcohols such as glycols, glycerine, diethylene glycol, pentaerythritol, sorbitol, mannitol, etc. which may optionally also be etherified, benzyl benzoate, dioxolanes, glycerol formals, tetrahydrofurfuryl alcohol, polyglycol ethers with $C_1$ to $C_{12}$ alcohols, dimethylacetamide, lactamides, lactates, ethyl carbonates, silicones (in particular medium viscous polydimethyl siloxanes), calcium carbonate, sodium carbonate, calcium phosphate, sodium phosphate, magnesium carbonate, gum arabic, alginic acid, stearates, fats and similarly acting substances.

In addition, the dosage forms may contain surface active substances that are active at the interface. Some examples that may be mentioned are: alkali soaps such as alkali salts of higher fatty acids (e.g. Na-palmitate, Na-stearate) or their derivatives (e.g. Na-ricinoleate sulfate); sulphurated compounds or sulphonated compounds which are formed by reaction of higher fatty alcohols with sulphuric acid or chlorosulphonic acid and are used, for example, as sodium salts (e.g. sodium lauryl sulphate, sodium acetyl sulphate, sodium stearyl sulphate, sodium acetyl sulphonate); salts of the gallic acids; saponins; quaternary ammonium compounds; partial fatty acid esters of sorbitan; partial fatty acid esters and fatty acid esters of polyoxyethylene sorbitans; sorbitol ether of polyoxyethylene; fatty acid esters of polyoxyethylene; fatty alcohol ethers of polyoxyethylene; fatty acid esters of saccharose; fatty acid esters of polyglycerol; proteins, lecithins.

The dosage forms may also contain celluloses, in particular if it is intended to prepare compressed shapes. These may be: purified cellulose (e.g. commercially available as Elcema ®) or microcrystalline celluloses as for example sold commercially under the name of Avicel ®. It is, however, also possible to use other filling agents having the function of binding agents such as calcium hydrogen phosphate, lactose, starches (e.g. potato starch, corn starch, modified starches such as Starch ST 1500/Colorcon), glucose, mannitol, saccharose.

The dosage forms may in addition contain sedimentation retardants such as for example highly disperse silicic acids having a surface of 50 to 500 $m^2/g$, in particular 100 to 400 $m^2/g$ (determined using the BET method). These are available commercially for example under the name Aerosil ®.

It may in addition be appropriate to use demolding agents in the dosage forms. Those that may be mentioned are: talcum or siliconized talcum, calcium- and magnesium stearate, stearic acid, paraffin, hydrated fats and oils, silicon oil emulsion.

Other auxiliary substances that may be used are substances that effect disintegration (so called disintegrants) such as: cross-linked polyvinyl pyrrolidone, sodium carboxymethyl starch, sodium carboxymethyl cellulose, formaldehyde gelatine, formaldehyde casein, polyacrylic acid and ultra-amylopectin.

To prepare solutions and suspensions it is for example possible to use water or physiologically acceptable organic solvents, for example ethanol, 1,2-propylene glycol, polyglycols and derivatives thereof. For injectable solutions or suspensions it is for example possible to use nontoxic parenterally tolerated diluting agents or solvents, such as for example: water, 1,3-butane diol, ethanol, 1,2-propylene glycol, polyglycol - water mixtures, Ringer's solution, isotonic salt solution.

Moreover the addition of stabilizers, colorants, antioxidants and complex formers (for example ethylenediaminetetra-acetic acid) and similar agents is possible as well as the addition of acids such as citric acid, tartaric acid, maleic acid, fumaric acid.

Antioxidants that may for example be used are sodium metabisulphite, cystein, ascorbic acid and their esters (for example palmitate), flavonoids, gallic acid, gallic acid alkyl esters, butylhydroxyanisol, nordihydroguaiacic acid, tocopherols as well as tocopherols+ synergists (substances which bind heavy metals by complex formation, for example lecithin, ascorbic acid, citric acid, phosphoric acid).

Preservatives or conserving agents that may be used are for example sorbic acid, p-hydroxybenzoic acid ester (e.g. lower alkyl esters), benzoic acid, sodium benzoate, trichloroisobutyl alcohol), phenol, cresol, benzethonium chloride and formalin derivatives.

Plasticizing agents that may be considered as coating substances are: citric and tartaric acid esters (acetyl-triethyl-, acetyl-, tributyl-, tributyl-, triethyl-citrate); glycerine and glycerine esters (glycerine diacetate, -triacetate, acetylated monoglycerides, castor oil); phthalic acid esters (dibutyl-, diamyl-, diethyl-, dimethyl-, dipropyl-, D-(2-methoxy- or ethoxyethyl)-phthalate, ethyl phthalyl- and butylphthalylethyl- and butylglycolate); alcohols (propylene glycol, polyethylene glycol of various chain lengths), adipates (diethyl-, di(2-methoxy- or ethoxy ethyl)adipate); benzophenone; diethyl- and dibutyl sebacate, -succinate, -tartrate; diethylene glycol dipropionate; ethylene glycol diacetate, -dibutyrate, -diproprionate; tributylphosphate, tributyrin; polyethylene glycol sorbitan mono-oleate; sorbitan mono-oleate.

To apply the sustained release components or coating substances it is possible to use solvents which may for example be aqueous solvents, alcohols, ketones, esters, ethers, aliphatic hydrocarbons, halogenated solvents, cycloaliphatic, aromatic or heterocyclic solvents or mixtures thereof. Typical solvents are inter alia acetone, diacetone-alcohol, methanol, ethanol, isopropyl alcohol, butyl alcohol, methylacetate, ethyl acetate, isopropyl acetate, n-butyl acetate, methylisobutyl ketone, methyl propyl ketone, n-hexane, n-heptane, ethyl glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene, toluene, naphtha, 1,4-dioxan, tetrahydrofuran, diethylene glycol dimethyl ether, water and mixtures thereof such as acetone and water, acetone and methanol, acetone and ethyl alcohol, methylene dichloride and methanol and ethylene dichloride and methanol and well as mixtures thereof. These solvents are removed again in the course of the coating process.

Independent of the process of preparation, the dosage forms of the invention are characterized in that they release the active substance azelastine or its physiologically acceptable salts at a release rate between 0.05 and 5 mg per hour to the body fluids or allow it to pass therein.

Dosage data relate in each case to azelastine as base; if azelastine salts are used, a conversion must be made according to the molecular weight.

The amounts of azelastine active substance in the formulations of the invention are
  a) for dosage forms to be used orally
0.1 mg to 50 mg, preferably
0.2 mg to 30 mg, in particular
0.5 mg to 20 mg of azelastine active substance.

The individual doses mentioned may be used 1–5, preferably 1–3, in particular 1–2 times daily.

b) in the case of dosage forms to be used parenterally (intravenously, intramuscularly, subcutaneously, intraperitoneally):
0.1 mg to 500 mg, preferably
0.2 mg to 400 mg, in particular
0.5 to 250 mg of azelastine active substance.

The single doses mentioned may be administered once monthly (for example for implants to be applied subcutaneously) up to 3 times daily, preferably once monthly to twice daily, in particular once monthly to once daily.

c) in the case of dosage forms to be used dermally (e.g. plasters)
5 mg to 5000 mg, preferably
10 mg to 3000 mg, in particular
30 mg to 2000 mg of azelastine active substance.

The single doses mentioned may be administered once daily to once monthly, preferably once every 3 days to once every 3 weeks, in particularly weekly to every 2 weeks.

Particularly preferred sustained release components are:
  a) Cation exchangers
  Sodium poly(styrene, divinylbenzene)sulphonate (e.g. Amberlite® IRP 69). 3 to 10 parts of Amberlite® IRP 69 are for example used per 1 part of azelastine (base).
  b) Coating substances
  Hydroxypropylmethyl cellulose phthalate
  1.5 to 3 parts of hydroxypropyl methyl cellulose phthalate 55 are used per 1 part of azelastine.
  Ethyl cellulose
  0.1 to 1 part of ethyl cellulose are used per 1 part of azelastine.
  Eudragit resins for example Eudragit®RS 0.01 to 0.1 part of Eudragit®RS per 1 part of azelastine.

c) Semi-permeable layers with osmotically acting active substance containing core and outlet openings: Coating with 100 to 300 μm thick layer of 82% cellulose acetate and 18% hydroxypropyl methyl cellulose.
  d) Embedding substances
  Hydrocolloids,74, e.g. hydroxypropyl methyl cellulose: 2 to 10 parts of hydrocolloid per 1 part of azelastine.
  Eudragit®RS:
  10 to 15 parts of Eudragit®RS per 1 part of azelastine. Glycerineditripalmito stearate (e.g. Precirol Ato 5) 1 to 10 parts of Precirol Ato 5 per 1 part of azelastine.

The requisite release of active substance of 0.05 to 5 mg per hour occurs within the desired range through the parameters described herein. Should it be desired to achieve a specific release rate within this range it is possible, for example, to proceed as follows:

1. The preparation of the coating or embedding of the active substance in the described manner.
2. Testing of the release of active substance from the dosage form using 0.1 N HCl (2 hours) and phosphate buffer pH 6.8 (subsequently) as release medium.
3. a) Should too much substance be released: Increase of the proportion of the sustained release component and/or reduction of the proportion of water-soluble auxiliary substances. Reduction of the proportion of osmotically active substance.
   b) Should too little substance be released: Reduction of the proportion of the sustained release component and/or increase of the proportion of water soluble auxiliary substances. Increase of the proportion of osmotically active substance.

In general it is preferred to achieve a release rate of 1 mg of azelastine per hour.

DETAILED DESCRIPTION OF PREFERRED EMBODIMENTS

EXAMPLE 1

100 g of azelastine hydrochloride are mixed with 960 g of hydroxypropyl methyl cellulose [viscosity of a 2% aqueous solution: 4000 cP (commercial product: e.g. Methocel K4M Premium)], 1320 g of spray-dried lactose and 20 g of magnesium stearate and the mixture pressed into tablets weighing 120 mg, having a diameter of 6 mm and a radius of curvature of 6 mm.

In conjunction therewith the tablets may be provided in a conventional procedure with a gastric juice-soluble or gastric juice permeable or gastric juice-resistant film coating.

To produce a gastric juice-resistant coating, 1000 g of tablets are sprayed with about 1000 g of the following suspension, for example in a coating drum:

63 g of cellulose acetate phthalate are dissolved in 480 g of acetone. To this solution are added 21 g of phthalic acid diethyl ester, 30 g of dichloromethane and 131 g of methanol. 4.4 g of titanium dioxide are suspended homogeneously in the solution obtained.

The spraying is carried out in discontinuous manner with heated air being blown in between the spraying phases for drying purposes.

One sustained release tablet contains 5 mg of azelastine hydrochloride.

EXAMPLE 2

12 g of azelastine hydrochloride, 20 g of Eudragit®RS PM, 250 g of talcum and 200 g of lactose are mixed and the mixture moistened with about 140 g of a mixture of 12.7 g of glycerine triacetate (commercial name for example Triacetin) and 127.3 g of Eudragit ® RS 12.5. The moist mass is granulated in a conventional manner through a sieve of mesh size 1 mm and sprayed, after drying at room temperature, in the coating drum onto a mixture of 909 g of Eudragit ®RS 12.5 and 91 g of Triacetin using a spray gun. The dried granulate so obtained is pressed into biconvex tablets weighing 300 mg each and having a diameter of 10 mm without addition of further auxiliary substances.

One tablet contains 5 mg of azelastine hydrochloride in sustained release formulation.

EXAMPLE 3

50 g of azelastine HCl are mixed with 100 g of tartaric acid, 250 g of lactose, 10 g of microcrystalline cellulose (Avicel PH 101) and 7 g of hydroxypropyl cellulose [viscosity of the 5% solution: 75 to 150 cps (e.g. trade name: Klucel LF)] and the mixture made up into a paste with 60 g of a 6.25% aqueous solution of hydroxypropyl cellulose (viscosity of the 5% aqueous solution: 75 to 150 cps (e.g. trade name Klucel LF)). The moist mass is pressed through a perforated plate having a hole diameter of 1 mm and the resulting strands are divided and rounded in the conventional manner by treatment on a spheronizer disc. The pellets obtained are dried and sieved. 300 g of pellets of the sieve fraction 800 to 1200 μm are coated in the conventional manner with a solution of 42.5 g of ethyl cellulose (trade name: Ethocel Type N 22), and 37.5 g of polyethylene glycol 1500 (trade name e.g. Carbowax 1540) in 720 g of chloroform through spraying in a fluidized bed apparatus.

50 mg of the above obtained coated pellets are filled into size 3 hard gelatin capsules.

One hard gelatin capsule contains 4.4 mg of azelastine hydrochloride in sustained release formulation.

EXAMPLE 4

The preparation of the dosage forms of the invention is effected by means of embedding in swelling agents: The following substances are mixed:

| (amounts in grams) Mixture | 1 | 2 | 3 |
|---|---|---|---|
| Azelastine hydrochloride | 50 | 50 | 50 |
| Hydroxypropyl methyl cellulose (= Methocel K 4 M) | 480 | 192 | 96 |
| Lactose | 660 | 948 | 1044 |
| Magnesium stearate | 10 | 10 | 10 |

The mixtures are pressed in a tablet press into planar tablets each weighing 120 mg and having a diameter of 6 mm.

| The thickness in mm is | 3.25 | 3.15 | 3.05 |
|---|---|---|---|
| Breaking strength (N) (Heberlein breaking strength tester) | 47 | 48 | 50 |

Each tablet contains 5 mg of azelastine HCl.

The release of active substance in the apparatus of USP XXI (dissolution tester apparatus 2, dissolution medium: 500 mg 0.1 N HCl, speed of rotation 120 rpm) is the following (release of active substance quoted in %):

| Mixture | 1 | 2 | 3 |
|---|---|---|---|
| After 5 mins | 4 | 31 | 50 |
| 60 mins | 20 | 76 | 100 |
| 120 mins | 36 | 96 | |
| 180 mins | 55 | | |
| 240 mins | 74 | | |
| 300 mins | 86 | | |
| 360 mins | 93 | | |

EXAMPLE 5

100 g of azelastine hydrochloride, 200 g of tartaric acid, 500 g of lactose and 700 g of microcrystalline cellulose are mixed and made up into a paste with about 700 g of purified water. The moist mass is pressed through a perforated plate of hole diameter 1 mm and the resulting strands are divided and rounded in a conventional manner on a spheronizer disc. The pellets obtained are dried and sieved.

1000 g of the pellets of sieve fraction 800 to 1250 μm are sprayed with a suspension which is prepared as follows:

0.6 g of Polysorbate 80 are dissolved in 190 g of purified water and 40 g of triethyl citrate are emulsified in the solution. 800 g of a 30% aqueous dispersion of a copolymerizate of acrylates and methacrylates with a low trimethylammonium ethacrylate chloride (=Eudragit ®RS 30 D) content are added to the emulsion obtained and stirred for about 10 minutes.

109.2 g of talcum and 0.2 g of silicon anti foaming oil (Simethicone) are suspended in 860 g of purified water. This suspension is stirred into the above obtained dispersion.

The coating of the lacquering suspension so obtained onto the pellets is effected in a conventional manner, for example using a fluidized bed spray granulator with an inlet air temperature of 40°-50° C. and a maximum outlet air temperature of 40° C. The drying of the pellets is effected under the same conditions.

The above mentioned lacquer suspension is sprayed on until the total weight of the dried pellets is equal to 1042 g.

The lacquered pellets are filled in amounts of 78.1 mg into size 3 hard gelatin capsules. Each hard gelatin capsule contains 5 mg of azelastine hydrochloride in sustained release formulation. The release of the active substance from a capsule in the apparatus of USP XXI (dissolution tester, apparatus 2, dissolution medium: 500 ml of 0.1 N HCl, rotation speed: 120 rpm) is:

| After 1 hour | 3.0 mg = 60% |
|---|---|
| After 2 hours | 4.5 mg = 90% |

The release of active substance is thus 3 mg per hour.

EXAMPLE 6

The procedure of Example 5 is followed, except that the lacquer suspension described in Example 5 is sprayed on until the total weight of the dried pellets is 1127 g. The lacquered pellets are then filled in amounts of 84.5 mg into size 3 hard gelatin capsules. Each hard gelatin capsule contains 5 mg of azelastine hydrochloride in sustained release formulation. The release of the active substance from a capsule in the apparatus of USP XXI is (conditions of the test as in Example 5):

| After 1 hour | 0.25 mg = 5% |
| After 2 hours | 0.50 mg = 10% |

The release of active substance is thus 0.25 mg per hour.

EXAMPLE 7

The procedure of Example 6 is followed.

If the pellets obtained in Example 6 are filled in amounts of 16.9 mg into size 3 hard gelatin capsules, each hard gelatin capsule contains 1 mg of azelastine hydrochloride in sustained release formulation. The release of the active substance from a capsule in the apparatus of USP XXI (conditions for the test as in Example 5) is:

| After 1 hour | 0.05 mg = 5% |
| After 2 hours | 0.10 mg = 10% |

The release of active substance is thus 0.05 mg per hour.

EXAMPLE 8

Capsules which contain 6 mg of Azelastine combined with a strong cationic exchange resin.

8.48 grams of azelastine hydrochloride is dissolved in 4 liters of distilled water. 71.5 grams of styrenesulfonic acid—divinylbenzene copolymer (degree of cross-linking 8% —a comercially available product, for example Amberlite ® IR 120) was suspended in this solution, and the suspension was agitated for 3 hours. The suspension was then filtered with a suction filter flask and the filter cake was washed twice with about 300 ml distilled water, after which the water was fully removed by suction.

5 grams of gelatin (isoelectric point 6-7.6, molecular weight 25,000-35,000—commercially available product: Gelita ® Collagel, Deutsche Gelatinefabriken, Eberbach/Neckar) is dissolved in a solution containg 5 grams of 1—normal hydrochloric acid solution in 800 grams of distilled water, in a glass beaker. The above-described filter cake is suspended in the solution and agitated for one hour. Next, the suspension was filtered with a suction flask and the filtercake is washed twice with about 200 ml of distilled water and the wash water is removed with suction.

The filter cake is dried at 60° C. The dried product is filled into size 4 hard gelatin capsules, 62 mg per capsule.

Each capsule contains 6 mg of azelastin, bound in a strongly acidic cation exchange resin.

EXAMPLE 9

A suspension which contains 6 mg Azelastine 5 ml of suspension, combined with a strong cationic exchange resin.

7.4 kg of distilled water is heated to 90°-95° C. and 0.002 kg propyl-4-hydroxybenzoate and 0.013 kg methyl-4-hydroxybenzoate were dissolved in the water. The solution is cooled to 70° C. and 0.020 kg hydroxyethyl cellulose (average degree of polymerization 250) and 3.0 kg suchrose are dissolved in it.

The solution is then cooled to 25° C. and 3 g rasberry flavor and 0.2 kg modified starch (Starch 1500 ®/Colorcon) are dissolved or suspended with stirring. 124 grams of the dried azelastin-containing ion exchange resin of Example 8 are then suspended in this medium with stirring. The suspension is finally made up to 11.0 kg with tilled water.

The effective rate of release from one of the capsules of Example 8 or from 5 ml of the suspension of Example 9 are determined in the apparatus of USP XXI (Dissolution test apparatus 2, dissolution medium 500 ml sodium chloride, 0.9%, rotation speed: 100 rpm), with the following results:

| After: | |
| --- | --- |
| 1 hour | 25% |
| 2 hours | 40% |
| 3 hours | 50% |
| 4 hours | 58% |
| 5 hours | 65% |
| 6 hours | 69% |
| 7 hours | 72% |
| 8 hours | 75% |

The dissolution medium was renewed every hour, the values for the released azelastine were added.

What is claimed is:

1. An azelastine-containing pharmaceutical composition which provides controlled release of azelastine which consists essentially of azelastine or a physiologically acceptable salt of azelastine as active ingredient and at least one sustained release component in an amount of 0.001 to 800 parts by weight of sustained release component for each part by weight of azelastine (calculated as base), the sustained release component and its amount being such that the release rate of azelastine from said composition is from 0.005 to 5 mg per hour when determined in an aqueous solution having a pH of 1.0 or a pH of 6.8.

2. An azelastine-containing pharmaceutical composition according to claim 1 in which the active substance azelastine or a physiologically acceptable salt thereof, optionally with addition of other conventional auxiliary and additional substances for controlled release
   a) is coated with one or more sustained release components, or
   b) is bound to a cation exchanger, or
   c) is reacted with one or more osmotically active substances and coated with a semi-permeable membrane and a hole is bored into the membrane, or
   d) is embedded in one or more substances of the group of digestible fats, indigestible fats, polymers or swelling agents, or is bound to these substances.

3. A dosage unit of an azelastine-containing pharmaceutical composition according to claim 1 suitable for oral administration in which the amount of azelastine is 0.1 to 50 mg.

4. A dosage unit of an azelastine-containing pharmaceutical composition according to claim 1 suitable for parenteral application in which the amount of azelastine is 0.1 to 500 mg.

5. A dosage unit of an azelastine-containing pharmaceutical composition according to claim 1 suitable for dermal application in which the amount of azelastine is 5 to 5000 mg.

6. A method of treating a patient in need of asthma prophylaxis or anti-allergic or antihistaminic treatment, said method comprising administering a dosage unit according to any one of claims 3 to 5.

* * * * *